United States Patent
Fukuyama et al.

(10) Patent No.: US 9,453,846 B2
(45) Date of Patent: Sep. 27, 2016

(54) MASS SPECTROMETRY METHOD USING MATRIX

(71) Applicants: SHIMADZU CORPORATION, Kyoto-shi, Kyoto (JP); NATIONAL UNIVERSITY OF CORPORATION HIROSHIMA UNIVERSITY, Higashihiroshima-shi, Hiroshima (JP)

(72) Inventors: Yuko Fukuyama, Kyoto (JP); Shunsuke Izumi, Higashihiroshima (JP)

(73) Assignees: SHIMADZU CORPORATION, Kyoto (JP); NATIONAL UNIVERSITY OF CORPORATION HIROSHIMA UNIVERSITY, Hiroshima (JP)

( * ) Notice: Subject to any disclaimer, the term of this patent is extended or adjusted under 35 U.S.C. 154(b) by 0 days.

(21) Appl. No.: 14/770,057

(22) PCT Filed: Mar. 4, 2014

(86) PCT No.: PCT/JP2014/055479
§ 371 (c)(1),
(2) Date: Aug. 24, 2015

(87) PCT Pub. No.: WO2014/136779
PCT Pub. Date: Sep. 12, 2014

(65) Prior Publication Data
US 2016/0011205 A1    Jan. 14, 2016

(30) Foreign Application Priority Data
Mar. 8, 2013   (JP) .................. 2013-046644

(51) Int. Cl.
*H01J 49/00* (2006.01)
*G01N 33/68* (2006.01)
(Continued)

(52) U.S. Cl.
CPC .......... *G01N 33/6851* (2013.01); *G01N 27/62* (2013.01); *G01N 27/64* (2013.01); *H01J 49/0027* (2013.01)

(58) Field of Classification Search
CPC .. G01N 33/6851; G01N 27/62; G01N 27/64; H01J 49/0027
USPC ........................................ 250/281, 282, 288
See application file for complete search history.

(56) References Cited

U.S. PATENT DOCUMENTS

2004/0119010 A1    6/2004  Perryman et al.
2005/0224710 A1   10/2005  Matsuo et al.
(Continued)

FOREIGN PATENT DOCUMENTS

EP    1 739 419 A1    1/2007
JP    6-322274 A     11/1994
(Continued)

OTHER PUBLICATIONS

Fukuyama, et al "Alkylated Trihydroxyacetophenone as a MALDI Matrix for Hydrophobic Peptides" Analytical Chemistry, 2013, vol. 85, pp. 9444-9448.*

(Continued)

*Primary Examiner* — Michael Maskell
(74) *Attorney, Agent, or Firm* — Cheng Law Group, PLLC

(57) ABSTRACT

The present invention provides a mass spectrometry method using a matrix that is capable of easily and efficiently improving ionization efficiency in mass spectrometry without modifying a molecule to be analyzed, and a matrix for mass spectrometry. A mass spectrometry method using, as a matrix, a 2,4,6-trihydroxyalkylphenone represented by the following general formula (I):

[Chemical Formula 1]

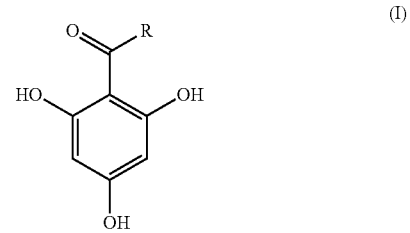

where R is an alkyl group having 4 to 12 carbon atoms. The mass spectrometry method as described above, wherein an analysis object is a hydrophobic compound, particularly, a hydrophobic peptide.

4 Claims, 3 Drawing Sheets

(51) Int. Cl.
*G01N 27/62* (2006.01)
*G01N 27/64* (2006.01)

(56) References Cited

U.S. PATENT DOCUMENTS

2006/0243899 A1  11/2006  Matsuo et al.
2012/0085903 A1   4/2012  Trimpin
2013/0062570 A1   3/2013  Fukuyama et al.

FOREIGN PATENT DOCUMENTS

| JP | 2005-326391 A | 11/2005 |
| JP | 2006-10672 A  | 1/2006  |
| JP | 2006-504971 A | 2/2006  |
| JP | 2012-529058 A | 11/2012 |
| JP | 2013-68598 A  | 4/2013  |
| JP | 2013-134102 A | 7/2013  |
| JP | 2013-190250 A | 9/2013  |

OTHER PUBLICATIONS

Supplementary European Search Report for the Application No. EP 14 76 0809 dated Oct. 12, 2015.

Pan, Chensong et al., "Recent developments in methods and technology for analysis of biological samples by MALDI-TOF-MS.", Analytical and Bioanalytical Chemistry, 2007, vol. 387, No. 1, pp. 193-204.

Jacksén, Johan et al., "Evaluation of 2,6-dihydroxyacetophenone as matrix-assisted laser desorption/ionization matrix for analysis of hydrophobic proteins and peptides.", Analytical Biochemistry, 2012, vol. 425, No. 1, pp. 18-20.

Fukuyama, Yuko et al., "Alkylated Dihydroxybenzoic Acid as a MALDI Matrix Additive for Hydrophobic Peptide Analysis.", Analytical Chemistry, 2012, vol. 84, No. 9, pp. 4237-4243.

International Search Report for the Application No. PCT/JP2014/055479 mailed Jun. 3, 2014.

Fukuyama, Yuko et al., "Alkyalated Trihydroxyacetophenone as a MALDI Matrix for Hydrophobic Peptides", Analytical Chemistry, 2013, vol. 85, pp. 9444-9448.

Browne, C. A. et al., "The Isolation of Peptides by High-Performance Liquid Chromatography Using Predicted Elution Postitions", Analytical Biochemistry, 1982, vol. 124, pp. 201-208.

Krokhin, Oleg V., "Sequence-Specific Retention Calculator, Algorithm for Peptide Retention Prediction in Ion-Pair RP-HPLC: Application to 300- and 100-Å Pore Size C18 Sorbents", Analytical Chemistry, 2006, vol. 78, pp. 7785-7795.

Written Opinion of the International Searching Authority (PCT/ISA/237) for Application No. PCT/JP2014/055479 mailed Jun. 3, 2014 (English Translation mailed Sep. 17, 2015).

\* cited by examiner

MASS SPECTROMETRY METHOD USING MATRIX

TECHNICAL FIELD

The present invention relates to a mass spectrometry method applicable to medical field and drug discovery field, and especially relates to MALDI-MS (Matrix-Assisted Laser Desorption/Ionization Mass Spectrometry) application. More precisely, the present invention relates to a mass spectrometry method using a specific compound as a matrix, and a matrix for mass spectrometry.

BACKGROUND ART

Conditions for achieving efficient ionization of a molecule to be analyzed in a MALDI (Matrix-Assisted Laser Desorption/Ionization) mass spectrometry method have been searched. For example, JP-A-2005-326391 (Patent Document 1) discloses a method in which a hydrophobic peptide is more efficiently ionized in mass spectrometry by previously modifying the hydrophobic peptide with a 2-nitrobenzenesulfenyl group and using, as a matrix, α-cyano-3-hydroxycinnamic acid (3-CHCA), 3-hydroxy-4-nitrobenzoic acid (3H4NBA), or a mixture of them than by using a common matrix such as α-cyano-4-hydroxycinnamic acid (4-CHCA) or 2,5-dihydrobenzoic acid (DHB).

PRIOR ART DOCUMENT

Patent Document

Patent Document 1: JP-A-2005-326391

SUMMARY OF THE INVENTION

Problems to be Solved by the Invention

According to the above MALDI mass spectrometry method, a certain level of ionization-promoting effect is obtained when modification of a molecule to be analyzed is performed, but sufficient ionization efficiency is not achieved when such modification is not performed. Particularly, the MALDI mass spectrometry method has a problem that the ionization efficiency of a molecular species difficult to be ionized by MALDI, such as a hydrophobic peptide, is low.

An object of the present invention is to provide a mass spectrometry method using a matrix that is capable of easily and efficiently improving ionization efficiency in mass spectrometry without modifying (specifically, labeling or the like) a molecule to be analyzed, and a matrix for mass spectrometry. Particularly, an object of the present invention is to provide a mass spectrometry method using a matrix that is capable of easily and efficiently improving ionization efficiency in MALDI mass spectrometry without modifying (specifically, labeling or the like) a molecule to be analyzed, and a matrix for MALDI mass spectrometry.

Means for Solving the Problems

The present inventors have intensively studied, and as a result, have found that a specific 2,4,6-trihydroxyalkylphenone functions as a matrix for use in a mass spectrometry method and can efficiently ionize a molecular species that is difficult to be ionized such as a hydrophobic compound. This finding has led to the completion of the present invention.

The present invention includes the following aspects.

(1) A mass spectrometry method using, as a matrix, a 2,4,6-trihydroxyalkylphenone represented by the following general formula (I):

[Chemical Formula 1]

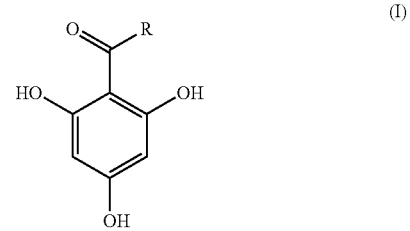

where R is an alkyl group having 4 to 12 carbon atoms.

(2) The mass spectrometry method according to (1), wherein an analysis object is a hydrophobic compound.

(3) The mass spectrometry method according to (1) or (2), wherein an analysis object is a hydrophobic peptide. In this specification, the term "peptide" includes proteins.

(4) The mass spectrometry method according to any one of (1) to (3), wherein R in the general formula (I) represents an alkyl group having 8 carbon atoms.

A matrix for mass spectrometry, which is a 2,4,6-trihydroxyalkylphenone represented by the following general formula (I):

[Chemical Formula 2]

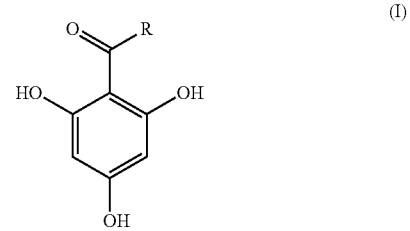

where R is an alkyl group having 4 to 12 carbon atoms.

The matrix for mass spectrometry described above, which is used for mass spectrometry of a hydrophobic compound.

The matrix for mass spectrometry described above, which is used for mass spectrometry of a hydrophobic peptide.

The matrix for mass spectrometry described above, wherein R in the general formula (I) represents an alkyl group having 8 carbon atoms.

Effects of the Invention

In the present invention, a 2,4,6-trihydroxyalkylphenone containing an alkyl group having 4 to 12 carbon atoms (R in the general formula (I)) is used as a matrix for mass spectrometry. The use of the 2,4,6-trihydroxyalkylphenone containing an alkyl group having 4 to 12 carbon atoms as a matrix for mass spectrometry makes it possible to improve the ionization efficiency of a molecular species that is difficult to be ionized such as a hydrophobic compound, especially a hydrophobic peptide. Therefore, the present invention provides a mass spectrometry method using a matrix capable of improving the ionization efficiency of a molecule to be analyzed, and a matrix for mass spectrometry. The present invention is particularly directed to a MALDI mass spectrometry method, and is suitable when an analysis object is a hydrophobic compound and particularly suitable when an analysis object is a hydrophobic peptide.

The present invention makes it possible to achieve improvement in sensitivity for detection of a molecule to be analyzed (especially, a hydrophobic peptide) in mass spectrometry measurement.

MODES FOR CARRYING OUT THE INVENTION

[Matrix]

Figure 1:
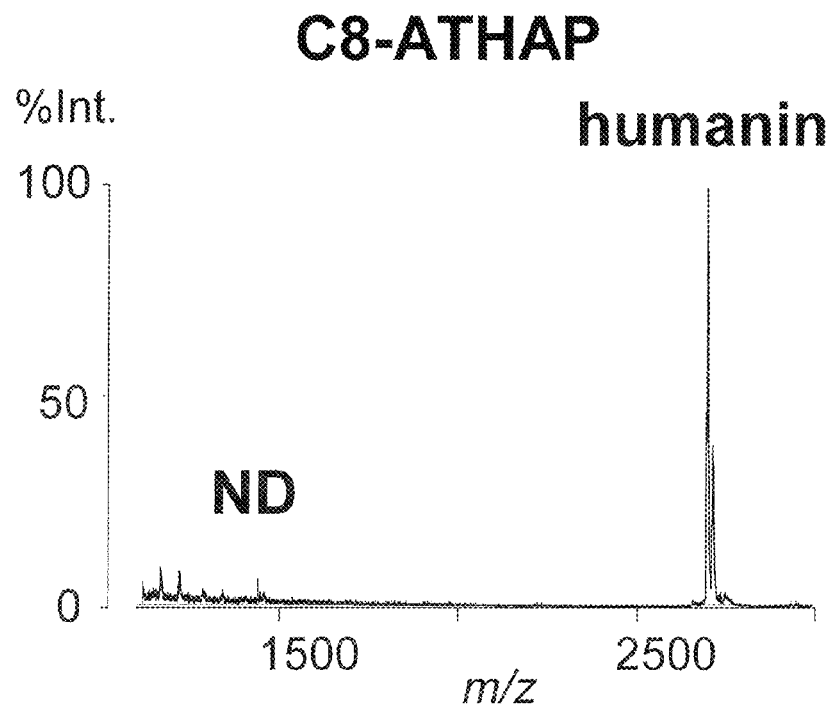
FIG. 1 is a mass spectrum of a mixture of a hydrophobic peptide Humanin and a hydrophilic peptide β-amyloid 1-11, which was obtained in Example 2 when C8-ATHAP was used as a matrix, wherein the horizontal axis represents mass/charge (m/z) and the vertical axis represents ion relative intensity (% Int.).

The present invention provides a mass spectrometry method using, as a matrix, a 2,4,6-trihydroxyalkylphenone represented by the following general formula (I). In the formula, R represents an alkyl group having 4 to 12 carbon atoms. In this specification, a compound represented by the general formula (I) (R=C4 to C12 alkyl group) may be referred to as ATHAP (Alkylated trihydroxyalkylphenone). For example, when R that is a C4 to C12 alkyl group is an octyl group (C8), a compound represented by the general formula (I) is referred to as C8-ATHAP. Further, 2',4',6'-trihydroxyacetophenone (R=CH$_3$ group) that is a compound falling outside the general formula (I) is referred to as THAP.

[Chemical Formula 3]

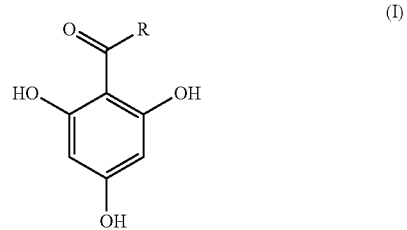

(I)

Examples of the C4 to C12 alkyl group represented by R in the general formula (I) include a butyl group, a pentyl group, a hexyl group, a heptyl group, an octyl group, a nonyl group, a decyl group, an undecyl group, and a dodecyl group. These alkyl groups may be either linear or branched. Examples of the branched C4 to C12 alkyl group include a 2-ethylhexyl group and the like. Among them, a C6 to C12 alkyl group is preferred, a C6 to C10 alkyl group is more preferred, and a C8 alkyl group is particularly preferred. When an analysis object is a hydrophobic compound, the alkyl group represented by R is considered to be required to have a certain level of hydrophobicity for the ionization of the hydrophobic compound.

In the present invention, the concentration of a matrix solution containing a matrix ATHAP represented by the general formula (I) (R=C4 to C12) may be, for example, 3 mg/mL to a saturation concentration. However, even when the concentration of the matrix solution is at a lower level within the above range, the ionization efficiency of an analysis object can be improved. For example, the concentration of the matrix solution may be about 1 mg/mL to 10 mg/mL, may also be about 1 to 8 mg/mL or about 1 to 5 mg/mL.

[Object to be Analyzed by Mass Spectrometry]

An object to be analyzed by mass spectrometry using the matrix according to the present invention is not particularly limited, and may be, for example, a molecule having a molecular weight of 500 to 30,000, preferably 1,000 to 10,000. The matrix according to the present invention can promote the ionization of a hydrophobic substance, and is therefore preferably used for mass spectrometry of a hydrophobic substance. In this case, a sample may contain a substance (e.g., a hydrophilic substance) other than the hydrophobic substance that is an analysis object. As shown in examples, the matrix according to the present invention can selectively promote the ionization of a hydrophobic substance without promoting the ionization of a hydrophilic substance as compared to a case where a conventional matrix α-cyano-4-hydroxycinnamic acid (4-CHCA) is used. Therefore, even when a sample contains both a hydrophobic substance and a hydrophilic substance in a mixture state, the hydrophobic substance can be easily analyzed. For this reason, the matrix according to the present invention can be appropriately applied to mass spectrometry of a hydrophobic substance.

The degree of hydrophobicity is not particularly limited as long as it is at a level that can be regarded as hydrophobic based on any known hydrophobicity index or hydrophobicity calculation method. For example, the degree of hydrophobicity of the hydrophobic substance may be at a level of hydrophobicity that can be regarded as hydrophobic by those skilled in the art based on the BB Index (Bull and Breese Index). More specifically, the BB Index of the hydrophobic substance may be, for example, 1,000 or less, preferably −1,000 or less.

Alternatively, the degree of hydrophobicity of the hydrophobic substance may be at a level that can be regarded as hydrophobic by those skilled in the art based on the HPLC Index. The HPLC Index is a hydrophobicity index reported by C. A. Browne, H. P. J. Bennett, S. Solomon in Analytical Biochemistry, 124, 201-208, 1982, and is also referred to as "HPLC/HFBA retention" because it is based on retention time in reversed-phase HPLC using, as an eluent, an aqueous acetonitrile solution containing 0.13% heptafluoro-n-butyric acid (HFBA). More specifically, the HPLC Index of the hydrophobic substance may be, for example, 40 or more, for example, 40 to 10,000, preferably 100 to 1,000.

Further, the degree of hydrophobicity of the hydrophobic substance in the present invention may be at a level that can be regarded as hydrophobic by those skilled in the art based on the SSRCalc Hydrophobicity. The SSRCalc Hydrophobicity is reported by Oleg V. Krokhin in Analytical Chemistry, 78, 7785-7795, 2006. The SSRCalc Hydrophobicity is a hydrophobicity index based on a peptide sequence-specific algorithm for retention times of peptides in RP-HPLC (Reversed-Phase High-Performance Liquid Chromatography), sequence-specific retention calculator (SSRCalc). The HPLC index or the BB index predicts a retention time based on only information about amino acid composition, whereas the SSRCalc Hydrophobicity predicts a retention time based on not only the primary structure but also the secondary structure of a peptide. In the present invention, when an analysis object is a hydrophobic peptide, the SSRCalc Hydrophobicity is suitable as an index of the degree of hydrophobicity. More specifically, the SSRCalc Hydrophobicity of the hydrophobic substance may be, for example, 30 or more, preferably 40 to 70.

In the present invention, the effect of enhancing the ability to ionize a hydrophobic peptide (in the present invention, the term "peptide" includes proteins) is particularly high. The determination as to whether a peptide to be analyzed is hydrophobic or not may be made based on the BB Index, the HPLC Index, or the SSRCalc Hydrophobicity, and preferably, the SSRCalc Hydrophobicity. Specifically, the hydrophobic peptide may be a peptide containing, as constituent amino acids, more amino acids having a higher degree of hydrophobicity. Examples of such hydrophobic amino acids include isoleucine, leucine, valine, alanine, phenylalanine, proline, methionine, tryptophan, and glycine. Further, cysteine, tyrosine, and the like may also be contained. The hydrophobic peptide may be a peptide having not only such a primary structure of the peptide but also a higher-order structure with a higher degree of hydrophobicity. Examples of such a hydrophobic peptide include peptides having a structure likely to interact with the surface of a hydrophobic stationary phase in a reversed-phase HPLC column.

[Formation of Crystal for Mass Spectrometry]

A crystal for mass spectrometry can be obtained through the step of forming, on a target plate for mass spectrometry, a liquid droplet of a mixture liquid containing, in a solvent, at least an analysis object and a matrix, and the step of removing the solvent from the formed liquid droplet of the mixture liquid to obtain non-volatile matter contained in the mixture liquid (i.e., at least the analysis object and the matrix) as a residue. Thus the obtained residue is a crystal for mass spectrometry. In this specification, the terms "crystal for mass spectrometry" is synonymous with the term "residue".

As the target for mass spectrometry, a conductive metal plate usually used for MALDI mass spectrometry can be used. Specifically, a plate made of stainless steel or gold can be used.

A specific method for preparing a liquid droplet of the mixture liquid on a target plate is not particularly limited. For example, first, a sample solution containing an analysis object and a matrix solution are prepared separately from each other. Then, these solutions are mixed to obtain a mixture liquid, and the obtained mixture liquid is dropped onto a target plate. Alternatively, these solutions are mixed on a target plate by dropping these solutions onto the same position on the target plate (on-target mix). In the case of on-target mix, the order of dropping the solutions is not particularly limited.

The solvent of the mixture liquid may be selected from the group consisting of acetonitrile (ACN), trifluoroacetic acid (TFA), methanol (MeOH), ethanol (EtOH), tetrahydrofuran (THF), dimethylsulfoxide (DMSO), and water. More specific examples of the solvent of the mixture liquid include an aqueous ACN-TFA solution, an aqueous ACN solution, an aqueous MeOH-TFA solution, an aqueous MeOH solution, an aqueous EtOH-TFA solution, an aqueous EtOH solution, an aqueous THF-TFA solution, an aqueous THF solution, an aqueous DMSO-TFA solution, and an aqueous DMSO solution. An aqueous ACN-TFA solution or an aqueous ACN solution may be more preferably used. The concentration of ACN in the aqueous ACN-TFA solution may be, for example, 10 to 90 vol %, preferably 25 to 75 vol %, and the concentration of TFA in the aqueous ACN-TFA solution may be, for example, 0.05 to 1 vol %, preferably 0.05 to 0.1 vol %.

The volume of the liquid droplet of the mixture liquid is not particularly limited, and may be appropriately determined by those skilled in the art. When a well is provided on the target plate, the liquid droplet of the mixture liquid may be formed in the well. In this case, the liquid droplet is formed so as to have a volume that can be held in the well. Specifically, the liquid droplet may be formed so as to have a volume of about 0.1 µL to 2 µL, for example, about 0.5 µL.

Then, the solvent is removed from the liquid droplet of the mixture liquid on the target plate. The removal of the solvent includes natural evaporation of the solvent. The amount of the matrix contained per one residue (that is, per one crystal for mass spectrometry) generated by evaporation may be, for example, 1 to 1,000 nmol, preferably 10 to 100 nmol. The amount of the analysis object may be in the range of, for example, 50 amol to 100 pmol or in the range of 100 amol to 50 pmol with respect to 10 nmol of the matrix.

The residue has a substantially circular shape on a surface in contact with the target plate. That is, the outer edge of the residue is substantially circular. The average diameter of the substantially circular shape may vary depending on the amount of the sample, the volume of the liquid droplet, the amount of the matrix, the composition of the solvent etc., but is for example 1 to 3 mm, preferably 1 to 2 mm. It is to be noted that the average diameter is the average of the lengths of line segments cut from lines passing through the center of gravity of the substantially circular shape by the outer edge of the residue.

In the substantially circular residue obtained by removing the solvent, the analysis object is uniformly present in a substantially circular manner. Therefore, ionization of the analysis object can be easily performed without positioning laser irradiation during ionization. The entire region of the residue can be regarded as a target for laser irradiation, which is advantageous for mass spectrometry measurement as compared to a case where a hydrophobic substance is localized in the outer edge region of the substantially circular residue (i.e., a hydrophobic substance is localized in a ring-shaped manner).

[Mass Spectrometer]

A mass spectrometer used in the present invention is not particularly limited as long as it is used in combination with a MALDI (Matrix-Assisted Laser Desorption/Ionization) ion source. Examples of such a mass spectrometer include MALDI-TOF (Matrix-Assisted Laser Desorption/Ionization-Time-of-Flight) mass spectrometers, MALDI-IT (Matrix-Assisted laser Desorption/Ionization-Ion Trap) mass spectrometers, MALDI-IT-TOF (Matrix-Assisted Laser Desorption/Ionization-Ion Trap-Time-of-Flight) mass spectrometers, and MALDI-FTICR (Matrix-Assisted Laser Desorption/Ionization-Fourier Transform Ion Cyclotron Resonance) mass spectrometers.

EXAMPLES

Hereinafter, the present invention will be described specifically with reference to examples, but is not limited to these examples.

Example 1

Evaluation of Detection Limits

In this example, each of compounds represented by the general formula (I), C6-ATHAP (R: n-hexyl group), C8-ATHAP (R: n-octyl group), C10-ATHAP (R: n-decyl group), and C12-ATHAP (R: n-dodecyl group) was used as a matrix.

(1) A 5 mg/mL solution (75% ACN/0.1% TFA water) (% is by volume; the same shall apply hereinafter) of each of the matrices C6-ATHAP, C8-ATHAP, C10-ATHAP, and C12-ATHAP was prepared.

(2) As sample solutions, 0.2 fmol to 2 pmol/µL solutions (50% ACN/0.1% TFA water) of a hydrophobic peptide Humanin were prepared.

(3) 0.5 µL of each of the sample solutions prepared in (2) and 0.5 µL of each of the matrix solutions prepared in (1) were dropped onto a MALDI target plate (MALDI plate: sample plate 2.8 mm ring×384 well (Shimadzu/Kratos, UK)) and mixed (on-target mix).

(4) Analysis was performed using AXIMA Performance (registered trademark) (SHIMADZU CORPORATION) by linear TOF in positive ion mode. Then, detection limits were evaluated.

Comparative Example (1) As matrix solutions, a 10 mg/mL solution (50% ACN/0.1% TFA water) of 4-CHCA (Laser Bio) and a 10 mg/mL solution (50% ACN/0.1% TFA water) of 2,4,6-trihydroxyacetophenone (THAP) were prepared.

(2) As sample solutions, 0.2 fmol to 2 pmol/µL solutions (50% ACN/0.1% TFA water) of a hydrophobic peptide Humanin were prepared.

(3) 0.5 µL of each of the sample solutions prepared in (2) and 0.5 µL of each of the matrix solutions prepared in (1) were dropped onto a MALDI target plate and mixed (on-target mix).

(4) Analysis was performed using AXIMA Performance (registered trademark) (SHIMADZU CORPORATION) by linear TOF in positive ion mode. Then, detection limits were evaluated.

Example 2

Analysis of Mixed Sample of Hydrophobic Peptide/Hydrophilic Peptide (1) As a matrix solution, a 5 mg/mL solution (75% ACN/0.1% TFA water) of C8-ATHAP was prepared. Further, as a matrix solution for comparative example, a 10 mg/mL solution (50% ACN/0.1% TFA water) of 4-CHCA was prepared.

(2) A 400 fmol/µL solution (50% ACN/0.1% TFA water) of a hydrophobic peptide Humanin and a 400 fmol/µL solution (50% ACN/0.1% TFA water) of a hydrophilic peptide β-amyloid 1-11 were mixed in a ratio of 1:1 (v/v) to prepare a sample mixture liquid (i.e., a solution containing 200 fmol/µL, of Humanin and 200 fmol/µL, of β-amyloid 1-11).

(3) 0.5 µL of the sample mixture solution prepared in (2) and 0.5 µL of the matrix solution or the matrix solution for comparative example prepared in (1) were dropped onto a MALDI target plate and mixed (on-target mix). That is, the amount of the sample Humanin per one well was 100 fmol/well, and the amount of the sample β-amyloid 1-11 per one well was 100 fmol/well.

(4) Analysis was performed using AXIMA Performance (registered trademark) (SHIMADZU CORPORATION) by linear TOF in positive ion mode.

Hydrophobic Peptide Humanin (BB Index: −5,800, HPLC Index: 117.4, SSRCalc Hydrophobicity: 50.0)

Hydrophilic Peptide β-amyloid 1-11 (BB Index: +2,510, HPLC Index: 1.4, SSRCalc Hydrophobicity: 13.5)

Figure 2:
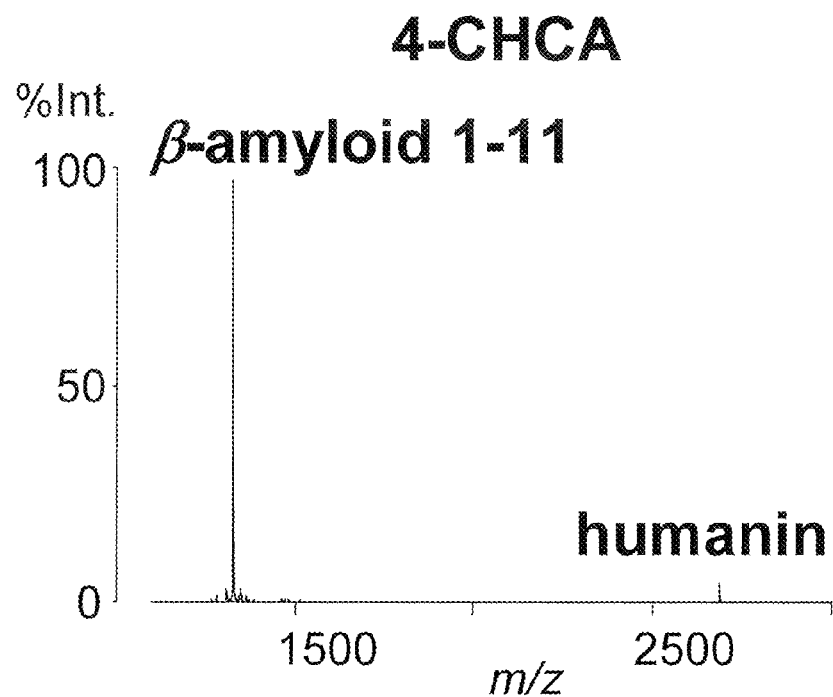
FIG. 2 is a mass spectrum of a mixture of a hydrophobic peptide Humanin and a hydrophilic peptide β-amyloid 1-11, which was obtained in Example 2 when 4-CHCA was used as a matrix.

FIG. 1 is a mass spectrum, which was obtained when C8-ATHAP was used as a matrix. FIG. 2 is a mass spectrum, which was obtained when 4-CHCA was used as a matrix. As shown in FIG. 2, when 4-CHCA was used as a matrix, both the hydrophobic peptide Humanin and the hydrophilic peptide β-amyloid 1-11 were detected, but rather, the hydrophilic peptide β-amyloid 1-11 was preferentially detected. On the other hand, as shown in FIG. 1, when C8-ATHAP was used as a matrix, the hydrophilic peptide β-amyloid 1-11 was not detected, and only the hydrophobic peptide Humanin was detected at high sensitivity. It is to be noted that "ND" in FIG. 1 means that no ion was detected.

These results showed that when C8-ATHAP was used as a matrix, MALDI ionization of the hydrophilic peptide β-amyloid 1-11 was not promoted or was inhibited, but MALDI ionization of the hydrophobic peptide Humanin was

TABLE 1

| | | Detection Limit (fmol/well) | | | | | |
|---|---|---|---|---|---|---|---|
| | | C6-ATHAP | C8-ATHAP | C10-ATHAP | C12-ATHAP | THAP | 4-CHCA |
| positive | humanin (hydrophobic peptide) | 10 | 1 | 10 | 10 | 10 | 10 |

As shown in Table 1, the detection limit when C6-ATHAP, C10-ATHAP, or C12-ATHAP was used as a matrix was the same as that when 4-CHCA or THAP was used. Particularly, it was confirmed that when C8-ATHAP was used, the detection limit was 1/10, that is, sensitivity was improved 10-fold as compared to when 4-CHCA or THAP was used.

promoted, and therefore only the hydrophobic peptide Humanin could be detected at high sensitivity.

It was confirmed that, as in the case of using C8-ATHAP as a matrix, also when C6-ATHAP, C10-ATHAP, or C12-ATHAP was used as a matrix, MALDI ionization of the hydrophilic peptide β-amyloid 1-11 was not promoted or was inhibited, but MALDI ionization of the hydrophobic peptide Humanin was promoted, and therefore only the hydrophobic peptide Humanin could be detected at high sensitivity.

Example 3

MS Imaging on Target Plate (1) As a matrix solution, a 5 mg/mL solution (75% ACN/0.1% TFA water) of C8-ATHAP was prepared.

(2) A 400 fmol/μL solution (50% ACN/0.1% TFA water) of a hydrophobic peptide Humanin and a 400 fmol/μL solution (50% ACN/0.1% TFA water) of a hydrophilic peptide β-amyloid 1-11 were mixed in a ratio of 1:1 (v/v) to prepare a sample mixture liquid (i.e., a solution containing 200 fmol/μL of Humanin and 200 fmol/μL of β-amyloid 1-11).

(3) 0.5 μL of the sample mixture solution prepared in (2) and 0.5 μL of the matrix solution prepared in (1) were dropped onto a MALDI target plate (MALDI plate: sample plate 2.8 mm ring×384 well (Shimadzu/Kratos, UK)) and mixed (on-target mix). That is, the amount of the sample Humanin per one well was 100 fmol/well, and the amount of the sample β-amyloid 1-11 per one well was 100 fmol/well.

(4) MS imaging was performed using AXIMA Performance (registered trademark) (SHIMADZU CORPORATION) by linear TOF in positive ion mode (raster: 4,000 μm×4,000 μm with 50 μm (81×81 lattice), 6,561 points). That is, MS imaging was performed by raster scanning an area of 4,000 μm×4,000 μm including the entire region of a residue on a well at an intervals of 50 μm (i.e., by automatically irradiating points in a certain region of a residue with laser at regular intervals) so that a total of 6,561 points (81×81 points) were irradiated with two shots of laser.

Figure 3:
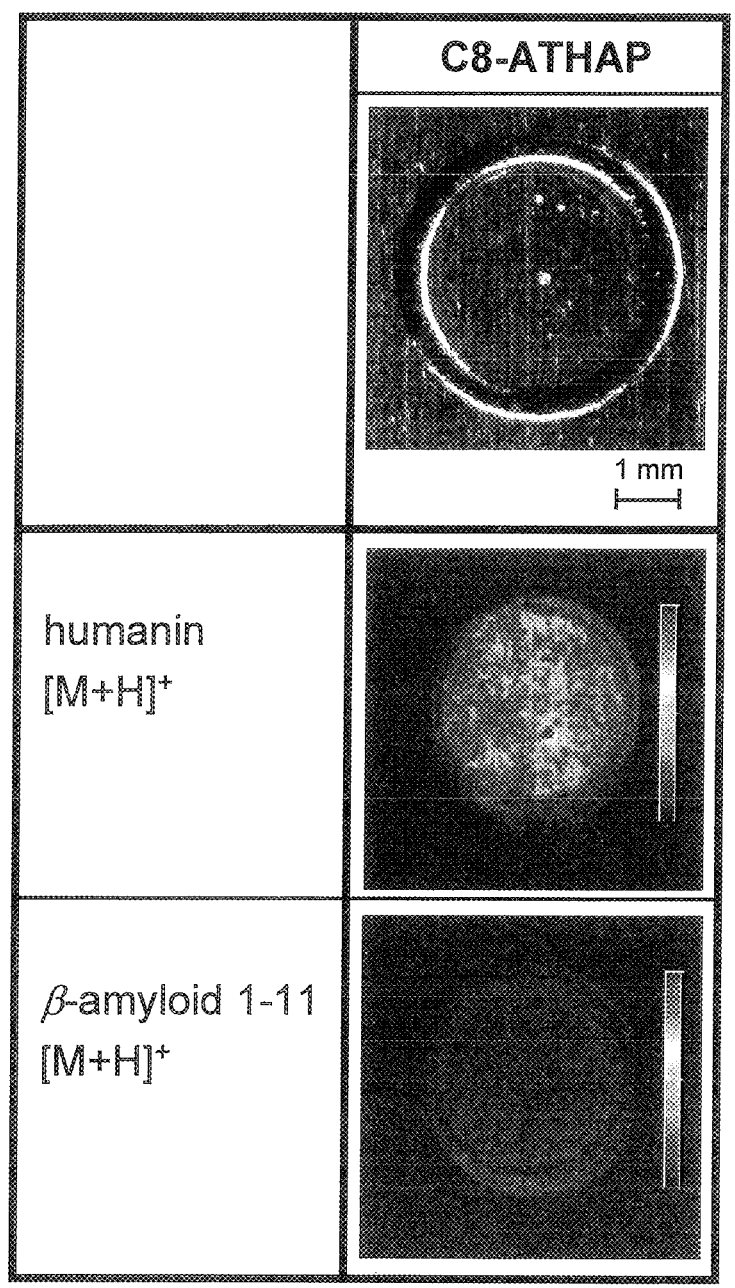
FIG. 3 shows a photograph of a crystal formed in a well on a MALDI plate, an MS image of the hydrophobic peptide Humanin, and an MS image of the hydrophilic peptide β-amyloid 1-11, in Example 3.

FIG. 3 shows a photograph of a crystal formed in a well on the MALDI plate, an MS image of the hydrophobic peptide Humanin in positive mode, and an MS image of the hydrophilic peptide β-amyloid 1-11 in positive mode.

As can be seen from FIG. 3, when C8-ATHAP was used as a matrix, the hydrophilic peptide β-amyloid 1-11 was not detected, and the hydrophobic peptide Humanin was relatively uniformly detected in the well.

Example 4

Evaluation of Detection Limits

In this example, C8-ATHAP (R in the general formula (I): n-octyl group) was used as a matrix to evaluate the detection limits of various peptides different in the degree of hydrophobicity.

(1) As a matrix solution, a 5 mg/mL solution (75% ACN/0.1% TFA water) of C8-ATHAP was prepared. Further, as a matrix solution for comparative example, a 10 mg/mL solution (50% ACN/0.1% TFA water) of 4-CHCA (Laser Bio) was prepared.

(2) As sample solutions, 0.2 fmol to 2 pmol/μL solutions (50% ACN/0.1% TFA water) of each of peptides NF-kB inhibitor, OVA-BIP hybrid peptide, Humanin, β-amyloid 22-42, catestatin, ACTH 18-39, nocistatin, neuropeptide S, β-amyloid 1-16, β-amyloid 1-11, and β-amyloid 165-178 were prepared.

(3) 0.5 μL of each of the sample solutions prepared in (2) and 0.5 μL of the matrix solution or the matrix solution for comparative example prepared in (1) were dropped onto a MALDI target plate (MALDI plate: sample plate 2.8 mm ring×384 well (Shimadzu/Kratos, UK) and mixed (on-target mix).

(4) Analysis was performed using AXIMA Performance (registered trademark) (SHIMADZU CORPORATION) by linear TOF in positive ion mode. Then, detection limits when each of the matrices was used were evaluated.

(5) The detection limit obtained using 4-CHCA was divided by the detection limit obtained using C8-ATHAP, and the obtained value was defined as sensitivity improvement rate (fold) achieved by C8-ATHAP.

Sensitivity improvement rate=[Detection limit obtained using 4-CHCA]/[Detection limit obtained using C8-ATHAP]

TABLE 2

| | analytes | | | |
|---|---|---|---|---|
| no. name | SSRCalc Hydrophobicity | HPLC Index | m/z (Ave.) | sensitivity improvement rate (fold) |
| 1 NF-κB inhibitor | 54.8 | 200.0 | 2782.6 | 10 |
| 2 OVA-BIP hybrid peptide | 50.2 | 100.8 | 2291.6 | 10 |
| 3 humanin | 50.0 | 117.4 | 2688.3 | 10 |
| 4 β-amyloid 22-42 | 42.4 | 44.5 | 2000.4 | 10 |
| 5 catestatin | 38.1 | 84.0 | 2327.7 | 1 |
| 6 ACTH 18-39 | 37.9 | 58.9 | 2466.7 | 1 |
| 7 nocistatin | 29.8 | 13.5 | 1928.1 | 1 |
| 8 neuropeptide S | 22.3 | 16.2 | 2188.5 | 0.1 |
| 9 β-amyloid 1-16 | 18.2 | −3.3 | 1956.1 | 0.1 |
| 10 β-amyloid 1-11 | 13.5 | 1.4 | 1326.3 | 0.001 |
| 11 β-conglycinin 165-178 | 5.2 | −60.2 | 1848.8 | 0.0001 |

As shown in Table 2, it was confirmed that when C8-ATHAP was used, the detection limits of the hydrophobic peptides having an SSRCalc Hydrophobicity of 42.4 or more were 1/10, that is, sensitivity was improved 10-fold as compared to a case where 4-CHCA was used.

On the other hand, as shown in Table 2, it was confirmed that when C8-ATHAP was used, the detection limits of the hydrophilic peptides having an SSRCalc Hydrophobicity of 22.3 or less were 10-fold to 10,000-fold, that is, sensitivity was reduced to 1/10 to 1/10,000 as compared to a case where 4-CHCA was used.

Example 5

Evaluation of Digests

In this example, C8-ATHAP (R in the general formula (I): n-octyl group) was used as a matrix.

(1) As a matrix solution, a 5 mg/mL solution (75% ACN/0.1% TFA water) of C8-ATHAP was prepared. Further, as a matrix solution for comparative example, a 10 mg/mL solution (50% ACN/0.1% TFA water) of 4-CHCA (Laser Bio) was prepared.

(2) As a sample solution, a solution containing Lys-C digests of a protein Phosphorylase b (2 pmol/μL) was prepared.

(3) 0.5 μL of the sample solution prepared in (2), and 0.5 μL of the matrix solution or the matrix solution for comparative example prepared in (1) were dropped onto a MALDI target plate (MALDI plate: sample plate 2.8 mm ring×384 well (Shimadzu/Kratos, UK)) and mixed (on-target mix).

(4) Analysis was performed using AXIMA Performance (registered trademark) (SHIMADZU CORPORATION) by linear TOF in positive ion mode. Then, a mass spectrum obtained using each of the matrices was evaluated.

(5) In Table 3, "++" indicates that a peptide ion was detected at S/N≥5 when C8-ATHAP or 4-CHCA was used as a matrix, "+" indicates that a peptide ion was detected at S/N=2 to 5 when C8-ATHAP or 4-CHCA was used as a matrix, and "−" indicates that a peptide ion was not detected when C8-ATHAP or 4-CHCA was used as a matrix.

Figure 4:
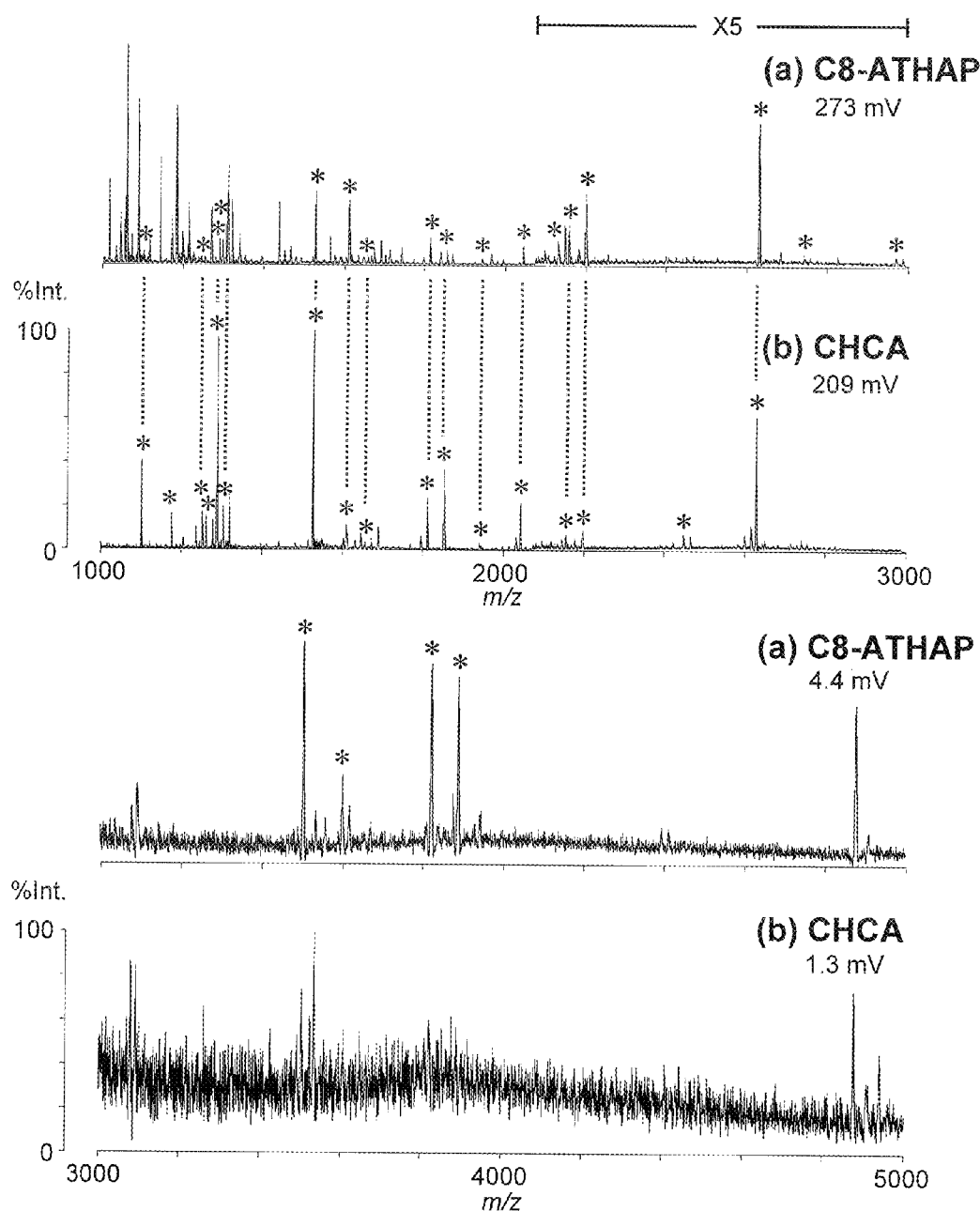
FIG. 4(a) is a mass spectrum obtained in Example 5 when C8-ATHAP was used as a matrix.
FIG. 4(b) is a mass spectrum obtained in Example 5 when 4-CHCA was used as a matrix.

FIG. 4(a) is a mass spectrum, which was obtained when C8-ATHAP was used as a matrix, and FIG. 4(b) is a mass spectrum, which was obtained when 4-CHCA was used as a matrix.

TABLE 3

| phosphorylase b Lys-C digests | | | | |
|---|---|---|---|---|
| no. | SSRCalc Hydrophobicity | HPLC Index | m/z (Ave.) | detection (+/−) |
| | | | | C8-ATHAP | CHCA |
| 1 | 55.9 | 142.3 | 3602.2 | ++ | − |
| 2 | 53.9 | 109.0 | 3823.5 | ++ | − |
| 3 | 53.1 | 102.5 | 3890.3 | ++ | − |
| 4 | 51.0 | 109.5 | 3823.5 | ++ | − |
| 5 | 50.7 | 78.4 | 2198.6 | ++ | + |
| 6 | 45.8 | 69.5 | 2155.6 | ++ | + |
| 7 | 45.1 | 46.2 | 2742.0 | + | + |
| 8 | 42.8 | 52.7 | 2969.5 | + | − |
| 9 | 38.9 | 56.8 | 3504.9 | ++ | − |
| 10 | 35.1 | 66.1 | 1855.1 | ++ | ++ |
| 11 | 33.9 | 37.5 | 1657.0 | + | + |
| 12 | 33.6 | 14.3 | 2130.5 | ++ | − |
| 13 | 33.4 | 61.6 | 2629.0 | ++ | ++ |
| 14 | 31.4 | 36.9 | 1610.9 | ++ | ++ |
| 15 | 31.4 | 31.2 | 1814.1 | ++ | ++ |
| 16 | 31.2 | 59.8 | 1526.8 | ++ | ++ |
| 17 | 30.9 | 43.7 | 2043.3 | ++ | ++ |
| 18 | 30.4 | 27.5 | 1942.3 | ++ | ++ |
| 19 | 29.9 | 36.3 | 2449.7 | − | + |
| 20 | 28.4 | 38.1 | 1304.7 | ++ | ++ |
| 21 | 25.8 | 24.5 | 1263.4 | − | ++ |
| 22 | 24.7 | 27.3 | 1178.3 | − | ++ |
| 23 | 24.5 | 44.1 | 1290.5 | + | ++ |

TABLE 3-continued

| phosphorylase b Lys-C digests | | | | |
|---|---|---|---|---|
| no. | SSRCalc Hydrophobicity | HPLC Index | m/z (Ave.) | detection (+/−) |
| | | | | C8-ATHAP | CHCA |
| 24 | 18.9 | 8.7 | 1254.5 | + | ++ |
| 25 | 9.3 | −0.7 | 1102.2 | − | ++ |

As shown in Table 3, when C8-ATHAP was used, peptides having an SSRCalc Hydrophobicity of 30.4 or more were detected, and when 4-CHCA was used, peptides having an SSRC Hydrophobicity of 33.4 or less were detected. That is, hydrophobic peptides that were not detected using 4-CHCA could be detected using C8-ATHAP.

The invention claimed is:

1. A mass spectrometry method using, as a matrix, a 2,4,6-trihydroxyalkylphenone represented by the following general formula (I):

[Chemical Formula 1]

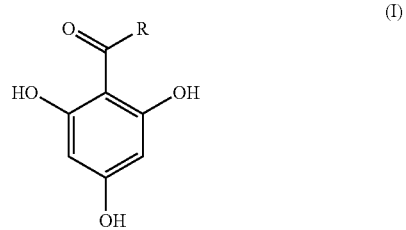

where R is an alkyl group having 4 to 12 carbon atoms.

2. The mass spectrometry method according to claim 1, wherein an analysis object is a hydrophobic compound.

3. The mass spectrometry method according to claim 1, wherein an analysis object is a hydrophobic peptide.

4. The mass spectrometry method according to claim 1, wherein R in the general formula (I) represents an alkyl group having 8 carbon atoms.

* * * * *